Dec. 9, 1958 P. ECKE Plant Pat. 1,780
POINSETTIA PLANT
Filed April 14, 1958
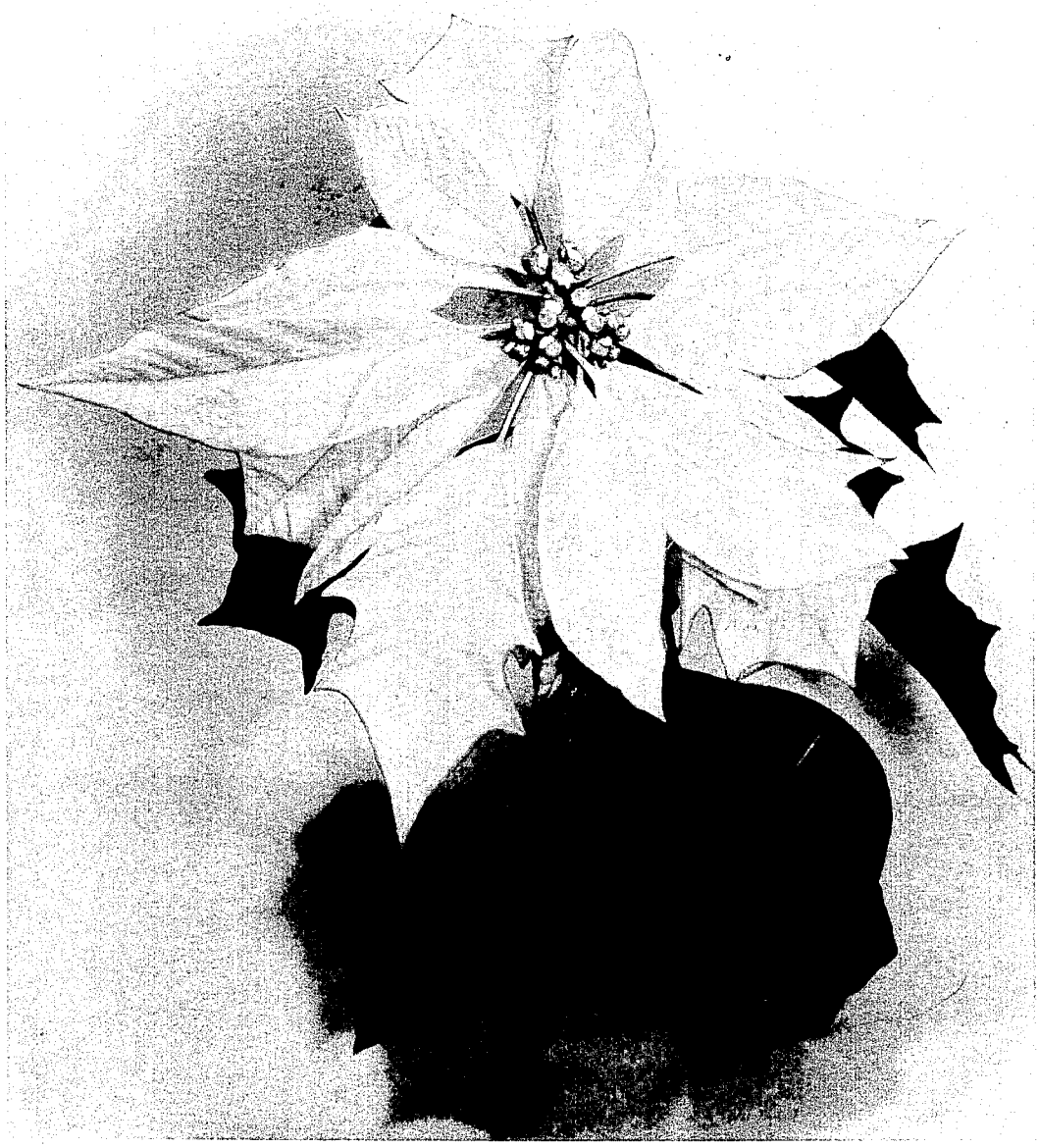
INVENTOR
Paul Ecke
by Wm. S. Graham
Attorney United States Patent Office Plant Pat. 1,780
Patented Dec. 9, 1958

1,780

POINSETTIA PLANT

Paul Ecke, Encinitas, Calif.

Application April 14, 1958, Serial No. 728,503

1 Claim. (Cl. 47—60)

The subject of the present invention or discovery is a new and distinct variety of poinsettia plant (*Euphorbia pulcherrima*) originating as a cultivated sport.

Broadly, this new variety of poinsettia plant is distinguishable from its parent plant, as well as from other known varieties, mainly in the vivid and intense rose-tinted red color of its bracts and their arrangement and heterogeneous configuration; and being further characterized in a more minor degree by its delayed maturity to optimum of its bract coloration, as well as the shortness of the internodes of its foliage leaves which gives it a lesser height than its parent plant.

The accompanying illustration forming a part of this application, graphically shows this new variety in color at full maturity or optimum, the illustration being a face view of the subject with its characteristics which differentiate this new variety.

The colors referred to herein correspond approximately with those shown in "Dictionary of Color" by Maerz and Paul (first edition, 1930), and identified by the common color name, and the plate of said color standard by recapitulation in tabular form herein.

The following is a detailed description of this new variety of poinsettia plant.

*Parentage*

This new variety was orginated as a cultivated sport and discovered by me in a cultivated area of a glass house or greenhouse at my experimental and growing gardens at Encinitas, San Diego County, California, its origin being a cultivated sport of poinsettia plant of the variety commonly known as "Barbara Ecke Supreme" poinsettia, which is patented in my Plant Patent No. 1,055 dated December 18, 1951.

*Propagation*

This new variety of poinsettia plant has been asexually reproduced and cultivated by me in my greenhouse or glass house, located at Encinitas, San Diego County, California, by cuttings and successive reproductions thereof have remained true to type and the herein described characteristics through asexual reproduction, cultivation and propagation through several generations, and its qualities and characteristics appear to be permanently fixed. In asexually reproducing this new variety I found it satisfactory and efficient to cut pieces of stalk of soft wood substantially six inches in length in the months of June, July and August, embedding one end of such cuttings in beds of sand in my glass house, and after three or four weeks the cuttings were well rooted and may be transferred to individual pots. My experience has been that the optimum temperature for growing under glass is of the order of sixty to sixty-five degrees F. night temperature, the daytime temperature being warmer and subject to the varying conditions of light, heating and thickness of glass, cultivation, character of soil, fertilizer and pruning or pinching.

*Habits of growth*

The plant will usually mature to optimum of its bracts in mid-December, usually having its maturity delayed from five to seven days beyond comparable maturity of its parent plant and other poinsettia plants of the red variety, a factor which is quite important in view of the relatively short season of greater demand for poinsettia plants. This variety retains its bracts and leaf foliage for substantially two months, after which the plant will normally go dormant for about three months until the following spring.

*Structure*

The peduncles which branch from the main trunk are usually relatively short, stiff and very strong, due, it is believed, to the fact that the internode space between foliage leaves is relatively short compared with other varieties, normally the height of the plant being from three to five feet, its height and luxurient growth depending appreciably on the type of pruning or pinching, cultivation and fertilization, all of which have a tendency to cause a growth of side shoots which provide a luxurient wide body growth relatively shorter in height than its parent plant and the other known varieties of red poinsettia plants. At the top end or axil of the peduncles a node is formed which grow stem-like bract-bearing branches or spurs, usually three in number, which bear the inflorescence and an involucre of bracts.

*Foliage leaves*

The foliage leaves are arranged around the peduncle, being more closely spaced than usual because of the relatively short inter-node between joints. As is characteristic of many types of poinsettia plants, the foliage leaves are not entirely uniform in shape, generally being oblate-ovate at the pedicel-end and having a plurality of oak-leaf points at the outer end. The petioles of the foliage leaves are relatively long and the venation is of herringbone type. The color of the foliage leaves may be broadly described as a mediumly dark ivy green.

*Bracts*

The bracts which are the predominating novelty of the present new variety are formed in an involucre or wreath radiating from the bract-bearing branches or spurs on relatively short petioles. They are not especially numerous in actual number comparable to some other varieties, but the individual bracts are relatively large in both width and length for the particular shape of bract which it typifies, the individual type of the separate bracts being varied by different shapes or types and the size thereof causing them to overlie relatively at adjacent edges in the nature of super-posed layers and forming an annular wreath having a small opening at its center surrounding the inflorescence.

The large bracts are generally elongated on the axis of the midrib but are varied in planar contour. Some of the bracts are prolately ovate-accuminate, others are definitely ovate accuminate, others are pinnatifid while others have the multi-accuminate edges typical of the oakleaf, while still others are of the rhomboidal-ovate type, making a tout ensemble both bizarre and optically aesthetic. It is not intended to say that every involucre of bracts of this new variety will produce all of the mentioned types of bracts, but rather to emphasize the pronounced eccentricity of planar shape of the several bracts. The bracts being elongated, provide a wide diameter to the involucre ranging up to six or seven inches.

Coupled with the eccentricity in shape of the individual bracts, they have a deep rich coloration of rose-tinted red closely parallel to a Chinese red, which, coupled with their irregularity of peripheral outline and close spacing around the inflorescence, provides a flaming burst of color unequalled in depth and richness by the bract involucre of any other variety of red poinsettia plant. The veining of the bracts is of the herringbone type.

The petioles of the bract are relatively short, thus drawing the bracts into close radiating relation to the inflorescence. They are of substantially the same color as the planar area of the bracts.

The season for optimum development of the bracts is from mid-December to approximately the end of December, maturing its vivid red color about five to seven days later than other known red varieties making this new variety a premium display plant for shipping and commercial sale at the height of the Christmas season.

*Inflorescence*

A node is formed at the upper axial end of each main stalk or peduncle, from which the bract-bearing branches or spurs grow upwardly and expansively apart, being usually three in number, and upon these branches or spurs grow a plurality of flower cyathia on short subacaulescent stems. Each cup-like cyathium is vase-like and contains a single pistillate flower surrounded by numerous staminate flowers, the pistillate flower pushing upward to the top where the stigma is spread for pollination. The cyathia are a pale green color at their base and the flowers are a lavender-red. Alongside of the cyathia are the nectary or nectar cups, the labial or open mouth of which is of an orange-yellow color.

*Immunity*

The entire plant seems to be immune or highly resistant to disease and all other obnoxious and detrimental influences, and under such conditions its growth is strong and luxurient, rendering cultivation and propagation relatively easy under favorable conditions which are normally exercised by those skilled in cultivation of poinsettia plants.

*Variations*

Different plants of this new variety have an unusual similarity of adherence to characteristics and type as herein described. However, in comparison of plants grown in various localities, in different soils, and at various times of the year, different temperatures and whether grown in greenhouses or out of doors, there may be variations of minor details.

*Color tabulation*

The color designations according to the color plates of said "Dictionary of Color" are recapitulated in tabular form as follows:

| Part of Plant | Non-Technical Designation of Color | Plate | Letter | Number |
|---|---|---|---|---|
| Foliage leaves | medium dark ivy green. | 23 | A | 12 |
| Bracts | rose-tinted red | 2 | L | 6 |
| Petioles of Bracts | do | 2 | L | 6 |
| Bract-bearing branches | pale green | 21 | L | 3 |
| Inflorescence: | | | | |
| Cyathia | do | 21 | L | 6 |
| Flowers | lavender-red | 51 | L | 3 |
| Labials of nectar cups | orange-yellow | 9 | L | 5 |

Having described and illustrated my new variety of poinsettia plant, I claim:

A new and distinct variety of poinsettia plant substantially as illustrated and described, characterized principally by an involucre of bracts of deep rich rose-tinted red color, and a variation in the shape of the planar contour of individual bracts in the involucre, the bracts having close grouping by relatively short petioles around the inflorescence, and the bracts being sufficiently numerous and of sufficient width to overlap at adjacent edges, whereby a wreath-like involucre of bracts is formed around the inflorescence.

No references cited.